United States Patent
Edens et al.

[11] Patent Number: 5,871,268
[45] Date of Patent: Feb. 16, 1999

[54] COOL WHITE LIGHT SOURCE

[75] Inventors: Roger A. Edens, Oconomowoc; Ronald L. Hueneke, Greendale, both of Wis.

[73] Assignee: Escalon Medical Corporation, Skillman, N.J.

[21] Appl. No.: 732,557

[22] Filed: Oct. 15, 1996

[51] Int. Cl.$^6$ .................................................. F21V 8/00
[52] U.S. Cl. ............................ 362/32; 362/293; 362/804
[58] Field of Search .................................... 362/321, 293, 362/276, 355, 804, 802

[56] References Cited

U.S. PATENT DOCUMENTS

| | | | |
|---|---|---|---|
| 4,082,946 | 4/1978 | Heine et al. | 362/32 |
| 4,385,344 | 5/1983 | Gonser | 362/32 |
| 4,415,952 | 11/1983 | Hattori et al. | 362/32 |
| 4,757,426 | 7/1988 | Scheller et al. | 362/20 |
| 4,855,875 | 8/1989 | Onose et al. | 362/32 |
| 4,870,952 | 10/1989 | Martinez | 128/23 |
| 5,003,434 | 3/1991 | Gonser et al. | 362/32 |
| 5,497,295 | 3/1996 | Gehly | 362/32 |
| 5,513,286 | 4/1996 | Easley | 385/19 |

*Primary Examiner*—Stephen Husar
*Attorney, Agent, or Firm*—Panitch Schwarze Jacobs & Nadel, P.C.

[57] ABSTRACT

A cool white light source includes a reflectorized lamp which outputs light having a correlated color temperature of about 5830° K., a first ultraviolet (UV) filter and a second infrared (IR) filter. The lamp reflector also acts as an initial IR filter and initially filters out about 80 percent or more of the infrared radiation spectrum of the lamp generated light before the lamp generated light is passed through the first UV filter and the second IR filter. The second IR filter has an effective filtration of about 90 percent at least above about 760 nm, suggestedly above about 720 nm and most desirably above about 700 nm. The UV filter has an effective UV reflectance of over 99 percent at least below about 375 nm and suggestedly below about 400 nm and desirably below about 420 nm. Since filtration occurs at the margins of the visible light spectrum, a high correlated color temperature is maintained, such that a balanced white light having a color temperature over 5000° K. is delivered.

26 Claims, 4 Drawing Sheets

COOL WHITE LIGHT SOURCE

FIELD OF THE INVENTION

The present invention relates generally to light sources and, more particularly, to apparatus for providing light which is non-toxic to human eyes.

BACKGROUND OF THE INVENTION

In order to perform ophthalmic surgery, adequate illumination of the eye is required. Such illumination is not adequately provided by a focused lamp located above the surgical area because the surgical field is within the eye. Rather, a beam of light is usually delivered to the surgical area with a fiber optic cable.

The quality of the light delivered to the surgical area is very important. In order to provide high clarity and vision in an anterior or posterior segment of the eye, it is preferred to deliver a bright, white light to the surgical area. The white light preferably does not include any hues which could make it difficult to distinguish areas within the eye. Typical light sources used in ophthalmic surgery have a correlated color temperature of about 3200° K. (Kelvin). In contrast, sunlight, the standard for white light, has a color temperature of about 6800° Kelvin. Such low color temperature lamps are used to avoid light toxicity to the eye. However, such low color temperature lamps do not provide a balanced white light, but rather the light includes red, orange or even yellow hues. The inclusion of such hues makes it difficult to view the retinal surface because a high percentage of the surface area of the retina is red. A light which includes a red hue brings out the red tissue of the skin, thereby making it harder to see subtle differences inside the eye. That is, visibility of the natural colors of the illuminated tissue is important for diagnostic purposes, and a color tinted light exacerbates the surgeon's ability to see the work area. Accordingly, it would be desirable to deliver a safe white light to a surgical area of the eye.

SUMMARY OF THE INVENTION

Briefly stated, the invention is a white light source for use by ophthalmic surgeons for illuminating an anterior or posterior segment of an eye and providing high clarity and vision thereof. The white light source comprises a source generating light having an ultraviolet spectrum component, an infrared spectrum component and a substantially continuous spectral distribution of visible light and a color temperature greater than 3500° K.; a first, ultraviolet (UV) radiation filter located to receive the light generated by the source and remove at least essentially all of the ultraviolet spectrum component of the generated light; and a second, infrared (IR) radiation filter positioned in series with the first filter to receive the light generated by the source and remove at least substantially all of the infrared spectrum component of the generated light toxic to ocular tissue, the light filtered by the first and second filters being at least essentially non-toxic to a human eye and having a color temperature of greater than 3500° Kelvin.

The invention also comprises a method of providing a white light for illuminating an anterior or posterior segment of an eye and providing high clarity and vision thereof. The method comprises the steps of:

providing a source for generating light having a relatively high color temperature;

filtering ultraviolet (UV) radiation from the light with a first filter;

filtering infrared (IR) radiation from the light with a second filter; and delivering the filtered light to a surgical area. The filtered light is substantially non-toxic to a human eye and has a color temperature greater than about 3500° K.

BRIEF DESCRIPTION OF THE DRAWINGS

The foregoing summary, as well as the following detailed description of preferred embodiments of the invention will be better understood when in conjunction with the appended drawings. For the purpose of illustrating the invention, there is shown diagrammatically in the drawings, embodiments which are presently preferred as well as other alternate embodiments. It should be understood, however, that the invention is not limited to the specific methods and instrumentalities disclosed. In the drawings.

DETAILED DESCRIPTION OF THE PREFERRED EMBODIMENTS

Figure 1:
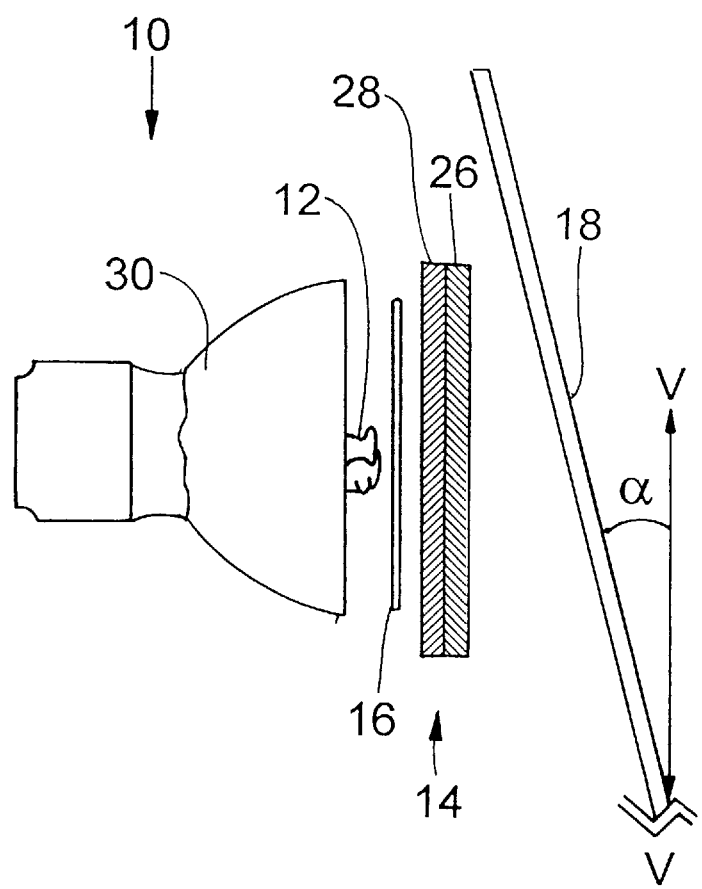
FIG. 1 is a partial side sectional view of a white light source in accordance with the present invention.

Certain terminology is used in the following description for convenience only and is not limiting. The words "top", "bottom", "lower" and "upper" designate directions in the drawings to which reference is made. The terminology includes the words above specifically mentioned, derivatives thereof and words of similar import.

Referring to the drawings, wherein like numerals are used for like elements throughout the several figures, there is shown in FIG. 1 an exploded side view of a white light source 10 in accordance with the present invention. The white light source 10 is advantageously used by ophthalmic surgeons for illuminating an anterior or posterior segment of an eye and providing high clarity and vision thereof. The white light source 10 comprises a source 12 which generates light, a filter system 14 for filtering predetermined spectral bands of radiation from the generated light, a diaphragm 16 for controlling transmission of the generated light, and a front panel 18 for facilitating delivery of the light to an area under observation, such as the anterior or posterior portion of an eye.

In order to perform microsurgery on portions of the eye, it is advantageous to deliver a balanced white light which does not contain any red, orange, or yellow hues. The delivered light must also be non-toxic to the eye. The purpose of the source of light 12 is to provide the best possible, near "daylight", illumination. Preferably the source of light 12 generates a substantially continuous spectral distribution of light in the spectral range having wavelengths at least between about 360 nm (nanometers) and about 800 nm. The correlated color temperature of the generated light should be at least 4500° K. before filtering if it is to provide improvement over existing sources having 3200° K. temperatures. In the presently preferred embodiment, the source of light 12 comprises a high intensity discharge lamp, such as a metal halide short arc lamp, which generates a relatively clear white light with a color temperature of about 5830° K. Such a lamp is generally commercially available. For instance, Welch Allyn of Skaneateles Falls, N.Y. supplies metal halide lamps, model nos. M24E001, M21E001 and M18E001, which produce a suitable white light with a substantially continuous spectral distribution of visible light and a relatively high color temperature. Although a metal halide lamp is preferred, it will be apparent to those of ordinary skill in the art that other lamps could be used with the present invention which also generate a relatively continuous band of visible light with a high color temperature, such as a tungsten halogen lamp or a xenon arc lamp.

Figure 2:
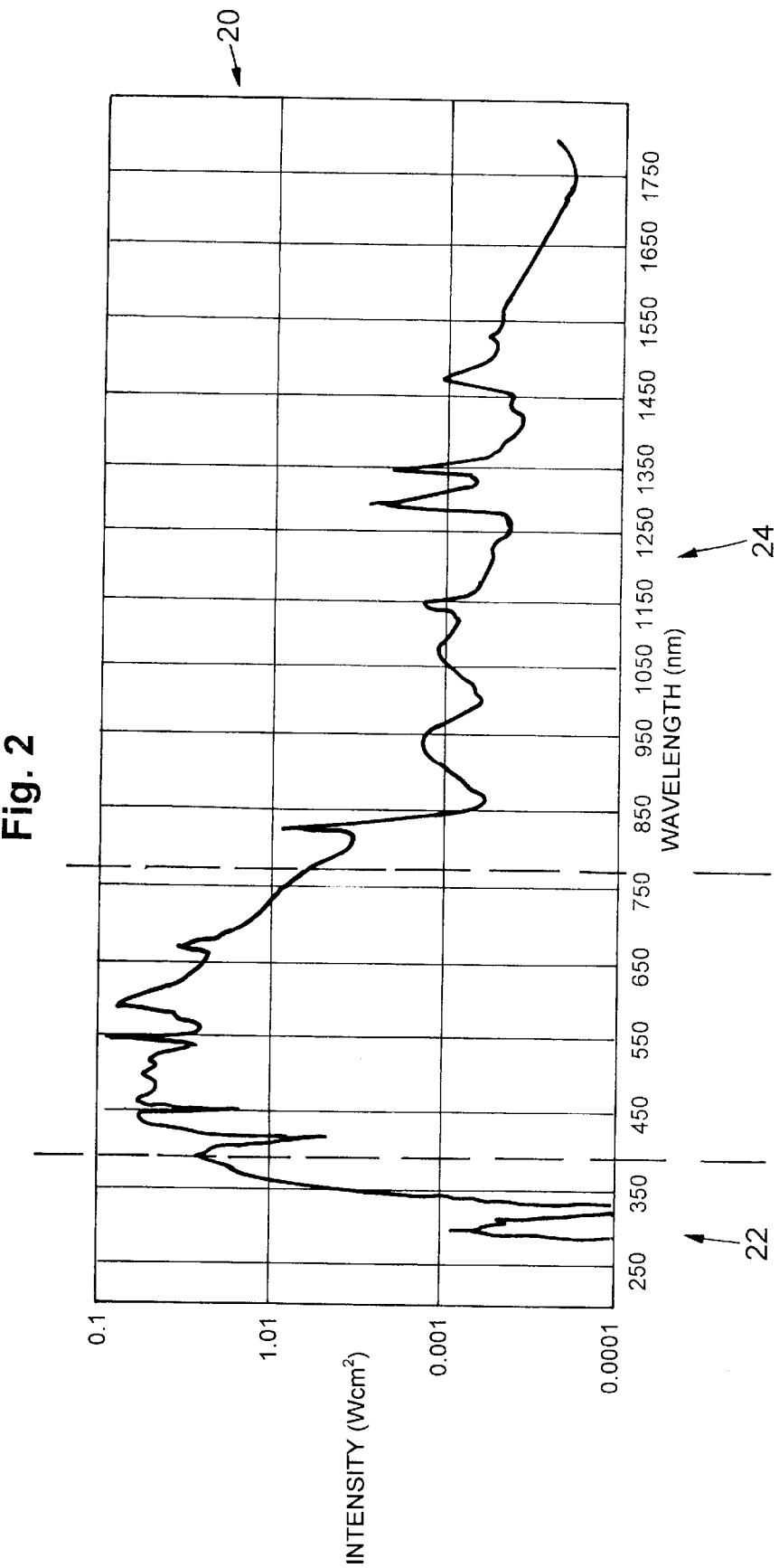
FIG. 2 is a graphic illustration of the spectral distribution of a source of light in accordance with a preferred embodiment of the present invention.

FIG. 2 is a graphic illustration of a spectral distribution 20 of the aforementioned model no. M21E001 metal halide lamp. FIG. 2 shows that the radiant energy produced by this lamp is continuous from about 330 nm to about 1800 nm. That is, there are no gaps or bands in this range where measurable light energy is not emitted. The spectral distribution 20 shows that the lamp generates a fair amount of radiation in both the near ultraviolet (UV) and near infrared (IR) spectrums, 22, 24, respectively.

Both UV and IR radiation can be harmful to the human eye tissue. According to an important aspect of the invention, these components are at least essentially eliminated prior to delivery of the light to a segment of the eye. Referring again to FIG. 1, the filter system 14 comprises a first filter 26 for filtering UV radiation from the generated light and a second filter 28 for filtering IR radiation from the generated light, such that the light filtered by both the first and second filters 26, 28 is at least essentially non-toxic to a human eye. However, in order to maintain the high color temperature (i.e. greater than 3500° K., desirably at least 4500° K. or more, and preferably more than 5000° K.), the filters 26, 28 do not significantly alter or reduce the color temperature of the generated light. The alteration should be less than twenty percent and preferably less than ten percent.

The UV spectral range includes wavelengths up to between about 360 to 400 nm. There are differing opinions as to the precise lower and upper boundaries of the visible light spectrum. There are also varying opinions as to the lower and upper boundaries of light wavelengths which are toxic to human ocular tissue. The spectral range of visible light wavelengths is from the upper end of the UV range to between about 700 to 760 nm. The IR spectral range of wavelengths extends upward from the upper end of the visible range.

The first, UV filter 26 should filter essentially all of the radiation having a wavelength less than 360 nm. An ultraviolet filter removing 99 percent or more of a light with wavelengths of 375 nm and less has been successfully used. However, under extreme conditions not normally encountered in ordinary ophthalmic use of such light sources, some retinal discoloration was noted. It is believed that 360 nm might be the lowest end of the light spectrum from the preferred light source (or from comparable light sources) that might be safely used within the human eye under at least some circumstances. There has been some concern expressed that even visible blue light near the UV end of the visible light spectrum can be toxic to ocular tissue under certain circumstances or to certain individuals. Therefore, 420 nm is believed to be the lowest end of the visible light spectrum that might be safely used under all circumstances.

A preferred UV filter uses "Schott" filter glass, as is known by those of skill in the art. Such a UV filter is provided by Andover Corp. of Salem, N.H., model no. 420FG03, which is a glass type filter with rated effective ultraviolet reflectance of over 99% of the total light generated by the source of light 12 at wavelengths of 420 nm and below. That is, only one percent or less of the light incident on the filter having wavelengths of 420 nm or less is passed by in the filter. Although a specific model no. and type of UV filter has been disclosed, it will be apparent to those of ordinary skill in the art that other UV filters are suitable for effectively filtering such UV radiation which is harmful to the human eye, which do not significantly alter the color temperature of the generated light.

The second IR filter 28 is used to eliminate light in the infrared spectrum (i.e. at least greater than 760 nm) harmful to ocular tissue. The preferred, second IR filter 28 has an effectiveness of greater than 90% with respect to light in the infrared spectrum and has at least such an effectiveness particularly with respect to wavelengths of at least about 760 nm and up. A suitable IR filter is provided by Andover Corp. of Salem, New Hampshire, model no. 775FW82, which is a hot mirror type IR filter. This device has an average transmittance greater than or equal to 85 percent for light with wavelengths between 450 to 675 nm and an average reflectance of greater than or equal to 90 percent for wavelengths between 750 and at least about 1200 nm. However, as with the first filter 26, it will be apparent to those of ordinary skill in the art that other IR filters are suitable for at least substantially removing from the generated light such IR spectrum component which is toxic to the human eye, without also significantly altering the color temperature of the generated light.

Either separate UV and IR filters can be used or a dual IR/UV filter could be used, such as a glass type UV filter with a laminate or coating thereon for filtering IR radiation. In an alternative embodiment, the first and second filters 26, 28 may comprise a single glass type UV filter with an IR coating having an average transmittance of greater than or equal to 85 percent over 450 to 655 nm and an average reflectance of greater than or equal to 90 percent over wavelengths from 730 to at least 1150 nm with a 50% cut-off at 690±10 nm. Such a filter can be obtained from Optical Corporation of America of Marlborough, Mass. The glass type UV filter passes no more than about one percent of light having a wavelength of 360 nm or less and preferably of light having a wavelength of 420 nm or less. It will be appreciated that such filters may be rated and available at 5, 10 or larger nanometer increments and that all have a transition range of wavelengths.

The first and second filters 26, 28 may be any size or shape. It will be understand by those of ordinary skill in the art that the size and relative positions of the filters 26, 28 with respect to each other is not critical and thus could differ from that shown in FIG. 1.

The preferred filter system 14 further comprises a reflector 30 integrally attached or mounted to the source of light 12. The reflector 30 reflects and focuses the light produced by the source of light 12. It will be noted by those of ordinary skill in the art that the preferred metal halide short arc lamp emits light out of the side of the lamp, and not out of the lamp ends. Therefore light is passed to the filters 26, 28 only by virtue of the presence of reflector 30. Lamp 12 and reflector 30 may also be considered to collectively constitute a source of light of the present invention.

In the preferred embodiment, the reflector 30 preferably comprises an elliptical reflector, and more preferably, a dichroic elliptical reflector which encompasses 360° (i.e. fully circumscribes) the light source 12. The reflector 30 both focuses the generated light and filters out about 80% of the infrared radiation of the generated light. The dichroic material of the reflector begins discernable transmission by about 700 nm and transmits at least about 80% or more of the IR spectrum beginning between 800 and 850 nm. Nearly 100% of the UV and visible spectrum below 700 nm is reflected and passed as generated light to filters 26, 28, by reflector 30. By transmitting only about 80% or more of the IR spectrum through the reflector 30 (and out the back of the reflector), only about 20% or less of the total IR spectrum energy is reflected and passed towards the first and second filters 26, 28. Thus, the reflector 30 is, in effect, a first IR filter. Although the second IR filter 28 provides only about 90% IR filtration, the second IR filter 28 is filtering about 20% or less of the total IR light output by lamp 12. That is, since the reflector 30 30 initially filters out about 80% of the infrared spectrum before the light reaches the second filter 28, the second IR filter only receives about 20% or less of the infrared energy generated by the light source 12. Therefore, the second IR filter 28, which filters about 90% of the remaining infrared energy, is adequate to rid the generated light of remaining toxic IR energy. The selected reflector 30 and the second IR filter 28 should collectively pass only about two percent or less of the infrared light above 760 nm originally generated by the source 12, suggestedly only about two percent or less of all infrared light above 720 nm and preferably only about two percent or less of all light above 700 nm. It will further be appreciated that the use of multiple infrared filters can help in dissipating heat created by the light source and that the 80 percent/90 percent filtering effectiveness of reflector 30 and IR filter 28 can be varied and still achieve the desired goal of passing no more than about two percent of the original infrared spectral component of light source 12 through the filters of source 10. Suggestedly, the reflector 30 is selected to remove more than half of the generated infrared light output from lamp 12 and desirably removes a significant portion (e.g. about ⅔ or more) of the infrared component.

Figure 3:
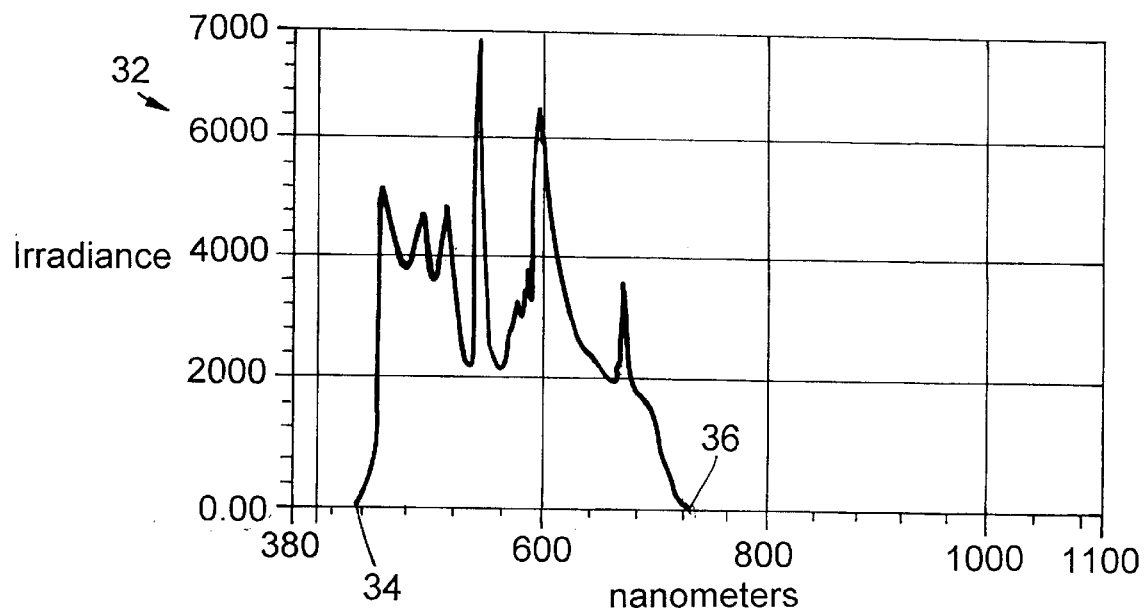
FIG. 3 is a graphic illustration of the spectral distribution of a filtered light in accordance with a preferred embodiment of the present invention.

Referring now to FIG. 3, a graphic illustration 32 of a spectral analysis of the white light source 10 in accordance with the present invention is shown. The graph 32 shows the measure irradiance in microwatts/cm² verses wavelength of the light delivered by the white light source 10 after the light generated by the source of light 12 is acted upon by the filter system 14. Total irradiance of the source of white light is about 972 milliwatts/cm² with an index of correlation of 88%. As indicated by the graph 32, the UV and IR spectrums are effectively filtered out. Remaining is visible light in the range from about 420 nm indicated at point 34 to about 720 nm indicated at point 36. This result was achieved using the Andover Corp. UV filter model no. 420FG03 with the Andover Corp. IR filter model no. 775FW82. With the Optical Corporation of America IR coating on the same UV filter glass, point 34 would be shifted down to about 700 nm. In addition, the color temperature of the delivered light is only slightly shifted down (shifted less than 10 percent) by the filter system 14 from about 5830° K. to about 5380° K. This temperature is still more than 5000° K. and therefore more than halfway between the correlated color temperatures of light sources previously used (e.g. 3200° K.) and sunlight (e.g. 6800° K.).

Figure 4:
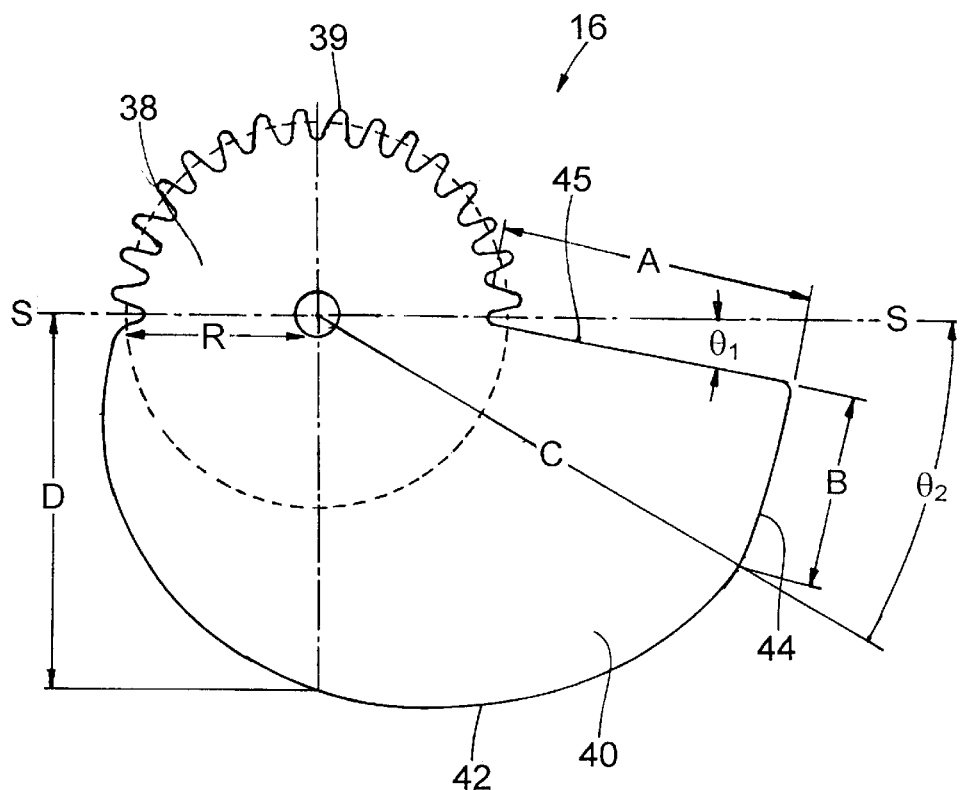
FIG. 4 is an enlarged plan view of a diaphragm in accordance with a preferred embodiment of the present invention.

Referring now to FIG. 4, an enlarged plan view of the diaphragm 16 is shown. The diaphragm 16 is provided to control transmission of the light generated by the source of light 12. The diaphragm 16 is preferably a linear type diaphragm which provides linear control of the light output. In the presently preferred embodiment, the diaphragm 16 comprises a preferably semicircular gear portion 38 with teeth 39 and a linear-helix portion 40 attached to or integral with the gear portion 38. The gear portion 38 extends through a circular arc of about 180°, (i.e., approximately half of one full rotation around the diaphragm), with the linear-helix portion 40 encompassing the remainder of the diaphragm 16. Rotation of the diaphragm 16 introduces a linear section 44 of the linear-helix portion 40 of the diaphragm 16 in front of the source of light 12, to control the amount of light passing the diaphragm 16. A gear connected to a separate shaft (neither shown) controls the rotation of the diaphragm 16, which in turn controls how much of the linear-helix portion 40 is positioned in front of the source of light 12 passing through the path of light from the source 12 through the filters 26, 28. As more of the diaphragm 16 is rotated in front of the source of light 12, less light is allowed to pass by the diaphragm 16.

The diaphragm 16 may be of any size or have any gear configuration, and may be made of any suitable materials, such as stamped metal or a polymeric material. In the presently preferred embodiment, the gear portion 38 of the diaphragm 16 has a radius R of approximately 0.50 inches and a 32 pitch per 20°, with a pitch diameter of 1.0 inch. The linear-helix portion 40 includes a perimeter with an arcuate, section 42, which extends from one end of the gear portion 38 to the linear section 44 of the perimeter, with the linear section 44 being connected to a second end of the gear portion 38 by an edge 45. The linear section 44 has a length B of approximately 0.50 inches. A distance from an outer periphery of the gear 38 to the linear perimeter section 44 is denoted as A, and is preferably approximately 0.84 inches. A distance from a center of the gear portion 38 to an outer periphery of the arcuate section 42, denoted at C, is preferably approximately 1.30 inches and the distance at D is preferably approximately 0.975 inches. The arcuate perimeter section 44 is located at an angle $\theta_1$ from a line S—S, which bisects the gear 38, and extends for an angle $\theta_2$ from the line S—S. Preferably, $\theta_1$ is approximately 10° and $\theta_2$ is approximately 30°.

Figure 5:
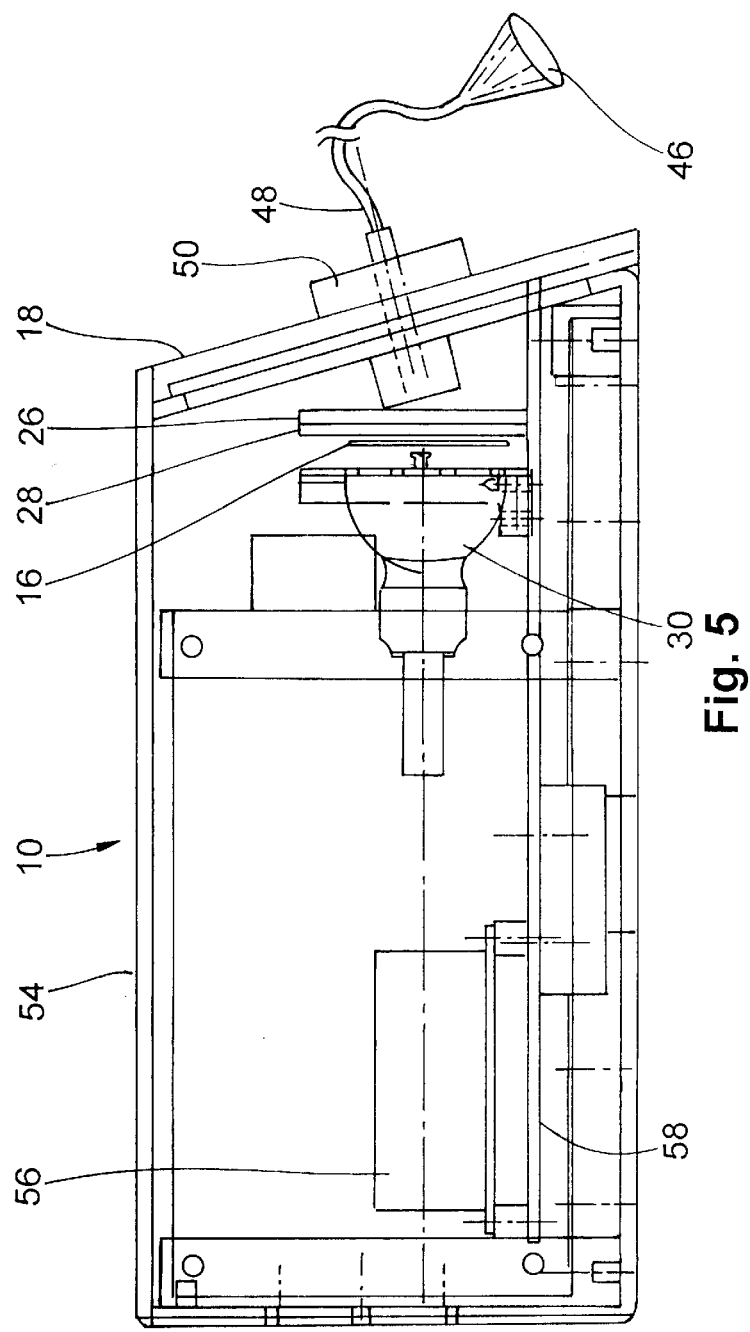
FIG. 5 is a side elevational view, partially in cross-section of the white light source, including a housing, in accordance with the present invention.

Referring now to FIG. 1 and FIG. 5, the front panel 18 facilitates delivery of the filtered light, shown at 46 (FIG. 5), to a work space or area under observation, such as the aforementioned anterior or posterior portion of a human eye. The front panel 18 preferably includes a front panel port assembly 50 for receiving one end, a proximal end, of a fiber optic cable 48. The filtered light 46 passed by the filters 26, 28 is focused on a proximal end of the fiber optic cable 48 such that the fiber optic cable 48 receives the filtered light 46 and delivers the filtered light 46 to the work space. That is, a focal point of the filtered light 46 is focused on the proximal end of the fiber optic cable 48. The fiber optic cable 48 is received within the front panel port 50 of the front panel 18 using a connector. The fiber optic cable 48 may be a plastic cable, which is disposable, such as an "intralux" style of fiber optic cable or adaptor. Such cables and connectors are generally known to those of ordinary skill in the art and further description of such a cable is not necessary for understanding the present invention.

Referring to FIG. 1, the front panel 18 is preferably disposed at an acute angle a with respect to the planes of the first and second filters 26, 28 and face of the light source 12 to facilitate and optimize the light quality and intensity transmitted through the first and second filters 26, 28 to the fiber optic cable 48. In FIG. 1, the angle α is shown with reference to a vertical line V—V parallel to the planes of filters 26, 28 and the face of the reflector 30 of light source 12.

Figure 6A:
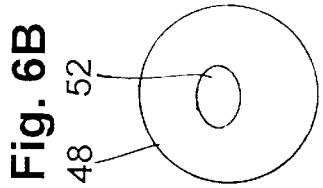
FIG. 6A is a cross-sectional view of a beam of light output from the white light source with a front panel at a 15° angle.
Figure 6B:
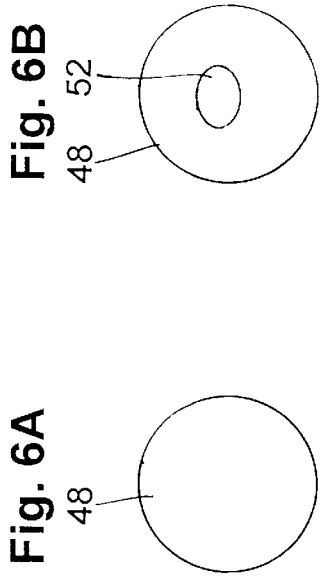
FIG. 6B is a cross-sectional view of a beam of light output from the white light source with a front panel in a vertical orientation.

Referring now to FIGS. 6A and 6B, placing the front panel 18 at an angle homogenizes the light focused on the fiber optic cable 48. FIGS. 6A and 6B show a typical light output with the front panel 18 at an acute, non-zero angle (α=15°) and straight on (α=0°), respectively. As shown in FIG. 6B, when the front panel 18 is not disposed at an acute angle to the plane(s) of the filter(s) and face of reflector 30 but is positioned at a zero angle, the light introduced to the fiber optic cable 48 includes a darkened region 52. Whereas in FIG. 6A, when the front panel 18 is disposed at an acute, non-zero angle to the plane(s) of the filter(s), the light introduced to the fiber optic cable 48 has a uniform distribution and does not include a darkened region. In the presently preferred embodiment, the acute, non-zero angle α is approximately 15° to the planes of filters 26, 28 and the face of the reflector 30 of light source 12.

Referring again to FIG. 5, the white light source 10 further comprises a housing 54 in which the source of light 12, the first and second filters 26, 28 and the diaphragm 16 are located. The housing 54 further preferably houses the electronic components, shown at 56, necessary to energize the source of light 12. Such electronic components 56 are generally well known to those of ordinary skill in the art and a detailed description thereof is not necessary for a complete understanding of the present invention. Preferably, the housing 54 interior is accessible to a user for maintenance, such as for changing or replacing a lamp bulb. For instance, the front panel 18 may be hinged and include a latch (not shown), thereby permitting the front panel 18 to be opened. In order to further facilitate access to the interior of the housing 54 and the electronic components 56, the source of light 12, and the first and second filters 26, 28, and other components located within the housing, such components may be located on or secured to a chassis 58 slidably disposed on a rail bearing which allows the chassis 58 to slide out of the housing 54.

An ophthalmic artificial light source apparatus has been disclosed for producing white light having a correlated color temperature of greater than 3500° K., and preferably greater than 5000° K. In a preferred embodiment, the light source comprises a metal halide lamp for producing light having a high color temperature and within a predetermined spectral bandwidth and a filter system which eliminate substantially all of the UV and IR radiation emitted by the lamp and which does not substantially reduce the color temperature of the light. The preferred light source delivers light with a color temperature of about 5380° K. and filtered of at least essentially all ultraviolet and infrared radiation components toxic to human ocular tissue. The UV and IR spectrums are so completely filtered out that the remaining light is essentially only in the visible spectrum.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A white light source for use by ophthalmic surgeons for illuminating an anterior or posterior segment of an eye and providing high clarity and vision thereof, the white light source comprising:
    a source generating light having an ultraviolet spectrum component, an infrared spectrum component and a substantially continuous spectral distribution of visible light and a color temperature greater than 3500° K.;
    a first, ultraviolet (UV) radiation filter located to receive the light generated by the source and remove at least essentially all of the ultraviolet spectrum component of the generated light; and
    a second, infrared (IR) radiation filter positioned in series with the first, ultraviolet filter to receive the light generated by the source and remove at least substantially all of the infrared spectrum component of the generated light toxic to ocular tissue, the light filtered by the first and second filters being at least essentially non-toxic to a human eye and having a color temperature of greater than 3500° Kelvin.

2. The white light source of claim 1 further comprising a reflector at least partially surrounding the light source, wherein the reflector initially filters out at least one-half of the infrared spectrum component of the generated light before the light passes to the first, ultraviolet filter and the second, infrared filter.

3. The white light source of claim 2 wherein the reflector fully circumscribes the light source.

4. The white light source of claim 2, wherein the reflector has an elliptical surface which reflects a remainder of the generated light.

5. The white light source of claim 2, wherein the reflector has a dichroic elliptical surface which reflects at least substantially all of the visible light spectrum component but only about 20% of the infrared spectrum component.

6. The white light source of claim 1 further comprising a linear style diaphragm movably mounted to intercept an optical path with the source and the first and second filters and control light output from the white light source.

7. The white light source of claim 6 wherein the diaphragm includes a toothed portion and a linear-helix portion and is supported such that rotation of the diaphragm by the toothed portion introduces a section of the linear-helix portion into a light path between the source and the diaphragm to control the amount of light passed by the diaphragm.

8. The white light source of claim 1 further comprising a fiber optic cable having a proximal end positioned to receive the generated light passed by both of the first and second filters.

9. The white light source of claim 8 further comprising a front panel and a front panel port assembly for receiving the proximal end of the fiber optic cable.

10. The white light source of claim 9 wherein at least one of the first and second filters is planar and the front panel is at about a 15° angle relative to the plane of the at least one filter.

11. The white light source of claim 10 wherein the first and second filters and a face of the source are parallel to a common plane and the front panel is at about a 15° angle relative to the common plane.

12. The white light source of claim 1 wherein the filtered light has a color temperature greater than 4500° K.

13. The white light source of claim 12 wherein the filtered light has a color temperature greater than 5000° Kelvin.

14. The white light source of claim 1 wherein the light passed by the first and second filters has a continuous spectral distribution only between about 375 nm and 760 nm.

15. The white light source of claim 1 wherein the light passed by the first and second filters has a continuous spectral distribution only between about 420 nm and 720 nm.

16. The white light source of claim 15 wherein the first and second filters comprises a glass type UV filter with an IR coating having a slope of about ±10 nm at a 50% mark with a transition starting point at about 690 nm.

17. The white light source of claim 1 wherein the light source comprises a metal halide short arc lamp.

18. The white light source of claim 1 wherein the first filter has an effective ultraviolet reflectance of about 99% or more up to wavelengths of about 375 nm.

19. The white light source of claim 1 wherein the second filter removes more than 90% of infrared red light incident on the second filter having wavelengths of 700 nm and more.

20. The white light source of claim 1 wherein the first and second filters together change the color temperature of the light from the source by less than twenty percent.

21. The white light source of claim 1 wherein the first and second filters change the color temperature of the light from the source by less than ten percent.

22. A white light source for use by ophthalmic surgeons for illuminating a segment of an eye and providing high clarity and vision thereof, the white light source comprising:

a source generating light having an ultraviolet spectrum component, an infrared spectrum component and a substantially continuous spectral distribution of visible light and a color temperature greater than 3500° K.;

a first, ultraviolet radiation filter located to receive the light generated by the source and remove substantially all of the ultraviolet spectrum component of the generated light toxic to ocular tissue; and a second, infrared radiation filter located to also receive the generated light received by the first, ultraviolet radiation filter and remove substantially all of the infrared spectrum component of the generated light toxic to ocular tissue, the second, IR filter comprising an elliptical reflector circumscribing the source and reflecting the generated visible light and the ultraviolet spectrum component and transmitting about 80% of the infrared spectrum component, and an IR filter positioned in series with the first, ultraviolet radiation filter to receive reflected light from the reflector, the IR filter removing substantially all of the remaining infrared spectrum component of the generated light toxic to ocular tissue, such that the light filtered by the first and second filters is essentially non-toxic to a human eye and has a color temperature of greater than 3500° Kelvin.

23. A method of providing a white light for illuminating an anterior or posterior segment of an eye and providing high clarity and vision thereof, comprising the steps of:

generating light having a continuous light spectrum and color temperature of greater than 3500° K. with a light source;

filtering ultraviolet (UV) radiation from the generated light with a first filter;

filtering infrared (IR) radiation from the generated light with a second filter; and delivering the UV and IR filtered light to a surgical area, wherein the first and second filters do not substantially change the color temperature of the generated light, and the filtered light is substantially non-toxic to a human eye and has a color temperature of greater than about 3500° K.

24. The method of claim 23 wherein the first filtering step comprises removing at least 99% of the generated light having wavelengths of 375 nm or less.

25. The method of claim 24 wherein the second filtering step comprises initially filtering the generated light with a reflector connected to a source of the light, the reflector filtering about 80% of an IR component of the generated light, and passing the reflector filtered light through a second IR filter removing at least 90° of any remaining infrared components of the reflector filtered light having wavelengths of 760 nm and higher.

26. The method of claim 24 wherein the surgical area comprises a human eye and the delivering step comprises delivering the filtered light to the eye with a color temperature greater than 5000° K.

* * * * *